(12) United States Patent
Oppenheimer

(10) Patent No.: US 8,822,730 B2
(45) Date of Patent: Sep. 2, 2014

(54) METHODS OF ISOLATING 4-CHLORO-2-FLUORO-3-SUBSTITUTED-PHENYLBORONIC ACIDS

(75) Inventor: Jossian Oppenheimer, Midland, MI (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/559,238

(22) Filed: Jul. 26, 2012

(65) Prior Publication Data

US 2013/0030213 A1    Jan. 31, 2013

Related U.S. Application Data

(60) Provisional application No. 61/511,867, filed on Jul. 26, 2011.

(51) Int. Cl.
*C07F 5/02* (2006.01)
*C07C 17/38* (2006.01)

(52) U.S. Cl.
CPC .................................... *C07C 17/38* (2013.01)
USPC ............................................................ 568/1

(58) Field of Classification Search
CPC combination set(s) only.
See application file for complete search history.

(56) References Cited

U.S. PATENT DOCUMENTS

| 7,300,907 | B2 | 11/2007 | Epp et al. |
| 7,314,849 | B2 | 1/2008 | Balko et al. |
| 7,538,214 | B2 | 5/2009 | Epp et al. |
| 7,611,647 | B2 * | 11/2009 | Arndt et al. ............... 260/665 R |
| 7,642,220 | B2 | 1/2010 | Epp et al. |
| 7,786,044 | B2 | 8/2010 | Epp et al. |
| 7,863,220 | B2 | 1/2011 | Clark et al. |
| 2008/0045734 | A1 | 2/2008 | Balko et al. |

FOREIGN PATENT DOCUMENTS

JP    2009-053165    3/2009
KR    10-0491163    5/2005

OTHER PUBLICATIONS

Of Osol et al., J. Am. Chem. Soc., 1933, 55 (11), pp. 4430-4440.*
Or "Crystallization and Precipitation" in Ullmann's Encyclopedia of Industrial Chemistry, John W. Mullin, Wiley-VCH Verlag GmbH & Co. KgaA, Published Online: Jan. 15, 2003, pp. 581-630.*
International Search Report and Written Opinion for PCT/US2012/048371, dated Feb. 1, 2013.

* cited by examiner

*Primary Examiner* — Karl J Puttlitz
(74) *Attorney, Agent, or Firm* — Robert Chang; TraskBritt P.C.

(57) ABSTRACT

Provided herein are methods of isolating a 4-chloro-2-fluoro-3-substituted-phenylboronic acid. The method comprises contacting a mixture of water, a water-miscible organic solvent, and a 4-chloro-2-fluoro-3-substituted-phenylboronic acid with a salt to form a water-miscible organic solvent layer and a water layer. The 4-chloro-2-fluoro-3-substituted-phenylboronic acid is partitioned into the water-miscible organic solvent layer, which is separated from the water layer. Additional methods are disclosed, as is a 4-chloro-2-fluoro-3-substituted-phenylboronic acid produced by one of the methods, wherein the 4-chloro-2-fluoro-3-substituted-phenylboronic acid is obtained at a yield of greater than approximately 90%.

17 Claims, No Drawings

METHODS OF ISOLATING 4-CHLORO-2-FLUORO-3-SUBSTITUTED-PHENYLBORONIC ACIDS

CROSS-REFERENCE TO RELATED APPLICATION

This application claims the benefit of U.S. Provisional Patent Application Ser. No. 61/511,867, filed Jul. 26, 2011, the disclosure of which is hereby incorporated herein in its entirety by this reference.

TECHNICAL FIELD

Embodiments of the present disclosure relate to methods of isolating a 4-chloro-2-fluoro-3-substituted-phenylboronic acid and especially to methods of isolating 4-chloro-2-fluoro-3-methoxyphenylboronic acid (PBA).

BACKGROUND

PBA and other 4-chloro-2-fluoro-3-substituted-phenylboronic acids are useful intermediates in the preparation of 6-(poly-substituted aryl)-4-aminopicolinate compounds and 2-(poly-substituted aryl)-6-amino-4-pyrimidinecarboxylic acid compounds, which are useful as herbicides. The PBA or other 4-chloro-2-fluoro-3-substituted-phenylboronic acids may then be esterified using 1,3-propanediol to form (4-chloro-2-fluoro-3-substituted phenyl)-[1,3,2]-dioxaborinane (PBE).

PBA may be synthesized by reacting 2-chloro-6-fluoroanisole (2,6-CFA) with n-butyllithium (n-BuLi) and an electrophilic boronic acid derivative. Following subsequent reactions, the PBA is isolated as a solid. For example, the PBA can be extracted from an aqueous phase using ethyl acetate and concentrated to dryness. Alternatively, the solid PBA can be isolated by a crystallization process. The solid PBA can then be utilized as an intermediate in a subsequent reaction to form the 6-(4-chloro-2-fluoro-3 methoxyphenyl)-4-aminopicolinate compound or 2-(4-chloro-2-fluoro-3 methoxyphenyl)-6-amino-4-pyrimidinecarboxylic acid compound.

More specifically, PBA may be synthesized by reacting 2,6-CFA with n-BuLi and trimethyl borate $B(OMe)_3$, adding an aqueous base to the reaction mixture, diluting the reaction mixture with acetonitrile ("MeCN"), and acidifying the reaction mixture with hydrochloric acid. The PBA can then be isolated by separating the MeCN and aqueous layers, providing an 80.3% yield of PBA.

BRIEF SUMMARY

An embodiment of the present disclosure includes a method of isolating a 4-chloro-2-fluoro-3-substituted-phenylboronic acid that comprises contacting a mixture of water, a water-miscible organic solvent, and the 4-chloro-2-fluoro-3-substituted-phenylboronic acid with a salt to form a water-miscible organic solvent layer and a salted water layer. The 4-chloro-2-fluoro-3-substituted-phenylboronic acid may be partitioned into the water-miscible organic solvent layer, which can be separated from the salted water layer.

Another embodiment of the present disclosure includes a method of isolating a 4-chloro-2-fluoro-3-substituted-phenylboronic acid that comprises adding a salt to an MeCN/water mixture including the 4-chloro-2-fluoro-3-substituted-phenylboronic acid. The 4-chloro-2-fluoro-3-substituted-phenylboronic acid may be partitioned into an MeCN layer, which can be separated from a water layer.

Yet another embodiment of the present disclosure includes a method of synthesizing and isolating 4-chloro-2-fluoro-3-methoxyphenylboronic acid (PBA) that comprises contacting 2,6-CFA with n-BuLi to form a lithiated derivative of 2,6-CFA. The lithiated derivative of 2,6-CFA may be contacted with $B(OCH_3)_3$ to form a boronic acid ester of 2,6-CFA. The boronic acid ester of 2,6-CFA can be contacted with aqueous sodium hydroxide to form a sodium salt of PBA. The sodium salt of PBA may be contacted with aqueous hydrochloric acid to form a solution of PBA. MeCN can be added to the solution of PBA to form a mixture of MeCN, water, and PBA. A salt may be added to the mixture of MeCN, water, and PBA to foam an MeCN layer and a water layer, which can be separated.

Yet still another embodiment of the present disclosure includes a 4-chloro-2-fluoro-3-substituted-phenylboronic acid produced by a process that comprises adding a salt to an MeCN/water mixture comprising a 4-chloro-2-fluoro-3-substituted-phenylboronic acid. The 4-chloro-2-fluoro-3-substituted-phenylboronic acid may be partitioned into an MeCN layer, which is separated from an aqueous layer. In particular embodiments, the yield of the 4-chloro-2-fluoro-3-substituted-phenylboronic acid is greater than approximately 90%.

DETAILED DESCRIPTION

Methods of isolating a 4-chloro-2-fluoro-3-substituted-phenylboronic acid, such as PBA, are disclosed. The 4-chloro-2-fluoro-3-substituted-phenylboronic acid may be synthesized by reacting a 3-chloro-1-fluoro-2-substituted benzene compound with an alkyl lithium compound, quenching the resulting lithiated benzene with an electrophilic boronic acid derivative reagent and hydrolyzing the resulting boronic acid derivative. The 4-chloro-2-fluoro-3-substituted-phenylboronic acid can be isolated from a mixture of water and a water-miscible organic solvent by adding a salt thereto. After separating layers of the water and water-miscible organic solvent, a solution of the 4-chloro-2-fluoro-3-substituted-phenylboronic acid in the water-miscible organic solvent is obtained. By adding the salt to the mixture of the water and water-miscible organic solvent, the yield of the 4-chloro-2-fluoro-3-substituted-phenylboronic acid may be improved. The solution of the 4-chloro-2-fluoro-3-substituted-phenylboronic acid may be used directly in additional reactions, such as a coupling or esterification reaction, without conducting additional acts, such as concentration or isolation acts. By eliminating recovery of the 4-chloro-2-fluoro-3-substituted-phenylboronic acid as a solid, the 4-chloro-2-fluoro-3-substituted-phenylboronic acid may be synthesized utilizing fewer unit operations.

A reaction scheme for the preparation of a 4-chloro-2-fluoro-3-substituted-phenylboronic acid from a 3-chloro-1-fluoro-2-substituted benzene compound, an alkyl lithium compound, and an electrophilic reagent is shown below:

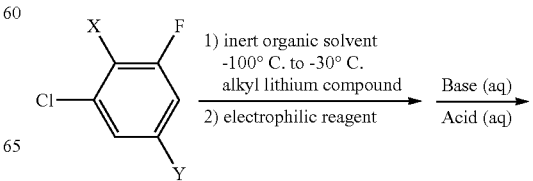

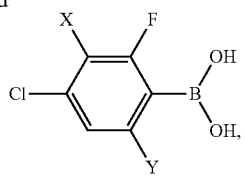

where X is F, OR$_1$, or NR$_2$R$_3$, Y is H or F, and each of R$_1$, R$_2$, and R$_3$ is independently a C$_1$-C$_4$ alkyl group. The alkyl group may be a straight chain, branched chain, or cyclic group including methyl, ethyl, 1-methylethyl, propyl, cyclopropyl, butyl, 1,1-dimethylethyl, cyclobutyl, 1-methylpropyl or 2-methylpropyl. The alkyl group may also be referred to as a normal (n), iso (i), secondary (s), or tertiary (t) alkyl group. The reaction product may be contacted with an aqueous base, followed by contact with an aqueous acid, to produce the 4-chloro-2-fluoro-3-substituted-phenylboronic acid.

In one embodiment, PBA is synthesized from 2,6-CFA by contacting the 2,6-CFA with n-BuLi and B(OMe)$_3$. A reaction scheme for the synthesis of PBA from 2,6-CFA, n-BuLi, and B(OMe)$_3$ is shown below:

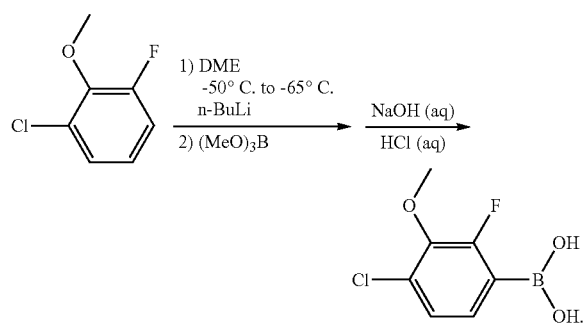

While various embodiments herein describe the synthesis and isolation of PBA from 2,6-CFA, n-BuLi, and B(OMe)$_3$, other 4-chloro-2-fluoro-3-substituted-phenylboronic acids may be synthesized in a similar manner by utilizing different starting materials.

To synthesize the PBA, 2,6-CFA or another 3-chloro-1-fluoro-2-substituted benzene compound may be contacted with the alkyl lithium compound, such as n-BuLi and the electrophilic reagent, such as B(OMe)$_3$, in a reaction vessel. The 2,6-CFA may be produced by conventional techniques, which are not described in detail herein. The reaction may be conducted in an inert organic solvent in which the 2,6-CFA is at least partially soluble. The inert organic solvent may be a C$_5$-C$_8$ straight-chain, branched, or cyclic hydrocarbon solvent, such as a pentane, a hexane, a cyclohexane, an isooctane, an ether, or combinations thereof. The ether may include, but is not limited to, diethyl ether, tetrahydrofuran, dioxane, or a glycol ether, such as 1,2-dimethoxyethane (DME). In one embodiment, the organic solvent is DME. The 2,6-CFA may be substantially soluble in the inert organic solvent, forming a 2,6-CFA solution in which the 2,6-CFA is substantially dissolved in the inert organic solvent. Methods of synthesizing PBA are disclosed in U.S. Pat. No. 7,611,647 B2, the contents of which are incorporated by reference herein.

The alkyl lithium compound may include, but is not limited to, MeLi, n-BuLi, or s-BuLi. In one embodiment, the alkyl lithium compound is n-BuLi. Alkyl lithium compounds are commercially available. At least one molar equivalent of the alkyl lithium compound may be used relative to the 2,6-CFA. To ensure complete reaction, the alkyl lithium compound may be added in a slight excess relative to the 2,6-CFA, such as from approximately 1% to approximately 10% molar excess relative to the 2,6-CFA, or from approximately 2% to approximately 5% molar excess relative to the 2,6-CFA.

The lithiation reaction with the alkyl lithium compound can be conducted under anhydrous conditions. The lithiation reaction may be conducted at a temperature of from approximately −100° C. to approximately −30° C. The 2,6-CFA solution may be cooled to, or maintained at, a temperature within this range before addition of the alkyl lithium compound. The reaction temperature may also be maintained within this temperature range during the addition of the alkyl lithium compound. The 2,6-CFA and the alkyl lithium compound may be allowed to react for a sufficient amount of time to deprotonate the 2,6-CFA while maintaining the reaction temperature within this temperature range. The reaction may be allowed to proceed, with stirring, until the deprotonation is substantially complete. The lithiation reaction may be conducted at atmospheric pressure or greater. The reaction may be conducted under an inert atmosphere, such as by flowing nitrogen (N$_2$) or other inert gas through the reaction vessel during the reaction.

The lithiation reaction can deprotonate the carbon atom of the 3-chloro-1-fluoro-2-substituted benzene compound at the open position adjacent to the 1-fluoro substituent. An intermediate compound in which lithium is bonded to the carbon atom adjacent to the 1-fluoro substituent is formed. The lithiated 3-chloro-1-fluoro-2-substituted benzene compound may then be contacted with the electrophilic reagent, which reacts at the C6 position of the 3-chloro-1-fluoro-2-substituted benzene compound. The electrophilic reagent, which functions as a source of the Z group, becomes bonded to C6 of the 3-chloro-1-fluoro-2-substituted benzene compound. The electrophilic reagent may be a trialkyl borate, such as B(OMe)$_3$. In one embodiment, the electrophilic reagent is B(OMe)$_3$, which reacts with C6 of the 3-chloro-1-fluoro-2-substituted benzene compound to produce a boronic acid ester. The reaction mixture including the lithiated 3-chloro-1-fluoro-2-substituted benzene compound may be cooled, such as from approximately −100° C. to approximately −30° C., before adding the electrophilic reagent. The electrophilic reagent may be added slowly, while maintaining the temperature of the reaction mixture at or below approximately −65° C. The reaction mixture may be allowed to react for an amount of time sufficient for the electrophilic reagent to react with the lithiated 3-chloro-1-fluoro-2-substituted benzene compound. During the reaction with the electrophilic reagent, the temperature of the reaction mixture may be allowed to slowly increase to room temperature (from approximately 20° C. to approximately 25° C.).

An aqueous base may be added to the reaction mixture at room temperature. The aqueous base may include a base of sufficient strength to hydrolyze the reaction product of the 3-chloro-1-fluoro-2-substituted benzene compound, the alkyl lithium compound and the electrophilic reagent. The base may include, but is not limited to, sodium hydroxide, potassium hydroxide, or combinations thereof. The aqueous base and the reaction mixture may be stirred for an amount of time sufficient for the base to hydrolyze the reaction product of the 3-chloro-1-fluoro-2-substituted benzene, the alkyl lithium compound, and the electrophilic reagent. The reaction mixture may then be transferred to a vessel in which the organic phase and the aqueous phase (aqueous base) separate into distinct layers, which are then separated. By way of example, the vessel may be a separatory funnel. The organic layer may be discarded, while the DME/water layer, which includes charged species of the reaction product of the 3-chloro-1-fluoro-2-substituted benzene, the alkyl lithium compound, and the electrophilic reagent, may be contacted with at least one volume of an organic solvent, such as t-butyl methyl ether (TBME), to remove unwanted organic impurities.

The aqueous layer, which includes the charged species of the reaction product of the 3-chloro-1-fluoro-2-substituted benzene, the alkyl lithium compound, and the electrophilic reagent, may be acidified and diluted with a water-miscible organic solvent. The aqueous layer may be acidified and then diluted with the water-miscible organic solvent, or may be diluted with the water-miscible organic solvent and then acidified. An aqueous acid may be added to the aqueous layer, protonating the charged species of the reaction product of the 3-chloro-1-fluoro-2-substituted benzene, the alkyl lithium compound, and the electrophilic reagent to produce the PBA or other 4-chloro-2-fluoro-3-substituted-phenylboronic acid. The acid of the aqueous acid should have sufficient strength to protonate the charged species. In one embodiment, the acid may be hydrochloric acid (HCl) and the aqueous acid includes 6 M HCl. An equimolar amount of the acid relative to the charged species of the reaction product of the 3-chloro-1-fluoro-2-substituted benzene, the alkyl lithium compound and the electrophilic reagent may be used. However, to ensure complete protonation, an excess of the acid may be used. Once protonated, the PBA or other 4-chloro-2-fluoro-3-substituted-phenylboronic acid may be substantially soluble in the water-miscible organic solvent relative to its solubility in the aqueous layer.

The aqueous layer, which includes the acidified reaction product of the 3-chloro-1-fluoro-2-substituted benzene, the alkyl lithium compound and the electrophilic reagent, may be diluted with the water-miscible organic solvent, such as MeCN. The water-miscible organic solvent may also be compatible with subsequent reactions to which the 4-chloro-2-fluoro-3-substituted-phenylboronic acid is subjected so that solvent exchange need not be conducted. While embodiments herein describe the water-miscible organic solvent as MeCN, other water-miscible organic solvents may be used. Since MeCN and water are substantially miscible, distinct aqueous and organic layers may not form. However, if the salt content of the MeCN/water mixture containing the acidified reaction product of the 1-fluoro-2-substituted-3-chlorobenzene, the alkyl lithium compound and the electrophilic reagent is sufficiently high, distinct aqueous and MeCN layers may form.

To isolate the PBA or other 4-chloro-2-fluoro-3-substituted-phenylboronic acids, a salt may be added to the MeCN/water mixture. The salt may be sodium chloride, potassium chloride, calcium chloride, sodium bromide, potassium bromide, sodium sulfate, potassium sulfate, ammonium chloride, or combinations thereof. For simplicity, a metal of the salt may be the same metal as the metal of the base used in the aqueous base. By way of example, if the base is sodium hydroxide, the salt may be a sodium salt. Similarly, if the base is potassium hydroxide, the salt may be a potassium salt. The addition of the salt may occur by adding a solid form of the salt directly to the MeCN/water mixture, or by adding an aqueous salt solution to the MeCN/water mixture. The aqueous salt solution may be a saturated solution of the salt in water. By way of example, if the salt is sodium chloride, the aqueous salt solution may be a brine solution, which includes from approximately 20% by weight to approximately 27% by weight of sodium chloride in water, such as approximately 25% by weight of sodium chloride. The brine solution may also be known as a saturated sodium chloride solution. Upon addition of the salt to the MeCN/water mixture, the salt may saturate the water, causing distinct aqueous and organic layers to form. Depending on the salt content of the MeCN/water mixture, two distinct layers may form without the addition of the salt. However, even if two distinct layers form, additional salt may be added to ensure the water is saturated with the salt. By maximizing the saturation of the water with the salt, recovery of the PBA or other 4-chloro-2-fluoro-3-substituted-phenylboronic acids from the MeCN/water mixture may be maximized. The addition of the salt may also cause the PBA or other 4-chloro-2-fluoro-3-substituted-phenylboronic acids to partition into the MeCN. The MeCN and the aqueous layer (aqueous solution) may be separated, with substantially all of the PBA or 4-chloro-2-fluoro-3-substituted-phenylboronic acid in solution in the MeCN. To recover any PBA or 4-chloro-2-fluoro-3-substituted-phenylboronic acid remaining in the aqueous solution, the aqueous solution may be contacted with additional volumes of MeCN. The multiple volumes of MeCN may then be combined, increasing the yield of PBA or 4-chloro-2-fluoro-3-substituted-phenylboronic acid obtained.

As shown in the detailed reaction scheme below, 2,6-CFA may be lithiated with n-BuLi in anhydrous DME, forming a lithiated derivative of 2,6-CFA (Li-2,6-CFA):

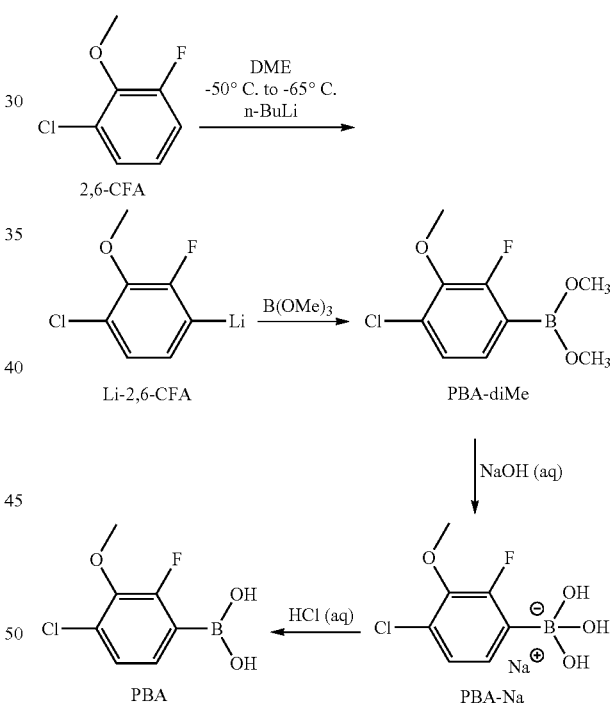

B(OMe)$_3$ may then be added and the reaction mixture slowly warmed to room temperature to form a boronic acid derivative (PBA-di Me) of Li-2,6-CFA. A solution of sodium hydroxide in water may be added at room temperature to the PBA-di Me, forming a charged, sodium derivative (PBA-Na) of PBA-di Me. After stirring, the PBA-Na may be transferred to a separatory funnel, where the aqueous and organic layers are allowed to separate. The aqueous layer may be washed with TBME to remove unreacted 2,6-CFA. The aqueous layer, which includes the PBA-Na, may be transferred to an Erlenmeyer flask, diluted with MeCN, and the mixture acidified by dropwise addition of 6M aqueous HCl, forming PBA. Alternatively, the aqueous layer including the PBA-Na may be acidified by dropwise addition of 6M aqueous HCl and then diluted with MeCN to form the PBA. Since MeCN is miscible with water, distinct aqueous and organic layers may not form. A saturated NaCl solution or NaCl solid may be added to assist in formation of the aqueous and organic layers by saturating the aqueous layer with salt. Depending on the salt content of the MeCN/water mixture, two distinct layers may form without the addition of the NaCl. However, even if two distinct layers form, additional NaCl may be added to ensure the aqueous layer is saturated with NaCl. The MeCN and aqueous layers may be separated, and the aqueous layer extracted with additional volumes of MeCN. To determine the yield of PBA or 4-chloro-2-fluoro-3-substituted-phenylboronic acid in the MeCN, the MeCN may be removed, such as by evaporation. The white solid obtained may be further dried in a vacuum oven to obtain a yield of greater than approximately 90% of the PBA or 4-chloro-2-fluoro-3-substituted-phenylboronic acid. The purity of the PBA or 4-chloro-2-fluoro-3-substituted-phenylboronic acid may be greater than approximately 90%, such as greater than approximately 95% or greater than approximately 98%. In comparison, if the PBA or 4-chloro-2-fluoro-3-substituted-phenylboronic acid is isolated from an MeCN/water mixture without adding a salt thereto, a lower yield of PBA or 4-chloro-2-fluoro-3-substituted-phenylboronic acid can be obtained, such as approximately 80% yield. Alternatively, the PBA or 4-chloro-2-fluoro-3-substituted-phenylboronic acid may remain in solution in the MeCN and may be used directly in subsequent reactions without further concentration or drying, thus reducing the number of unit operations in the overall process. The yield of the PBA in this case is determined by GC using an internal standard.

By way of example, the solution of PBA or 4-chloro-2-fluoro-3-substituted-phenylboronic acid in MeCN may be utilized in a Suzuki coupling reaction. The PBA or 4-chloro-2-fluoro-3-substituted-phenylboronic acid may be esterified with 1,3-propanediol in MeCN to produce (4-chloro-2-fluoro-3-methoxyphenyl)-[1,3,2]-dioxaborinane (PBE) in good yield, such as greater than or equal to approximately 95%. The PBE in MeCN may also be used directly in the Suzuki coupling reaction without first producing PBE. The Suzuki coupling reaction is known in the art and, therefore, is not described in detail herein. The PBE may be used, for instance, as an intermediate in the formation of 6-(4-chloro-2-fluoro-3 methoxyphenyl)-4-aminopicolinate compounds or 2-(4-chloro-2-fluoro-3 methoxyphenyl)-6-amino-4-pyrimidinecarboxylic acid compounds, which are useful as herbicides. The conversion of PBE to 6-(4-chloro-2-fluoro-3 methoxyphenyl)-4-aminopicolinate compounds or 2-(4-chloro-2-fluoro-3 methoxyphenyl)-6-amino-4-pyrimidinecarboxylic acid compounds is known in the art and, therefore, is not described in detail herein.

While saturated salt solutions have been used in liquid/liquid extractions, the saturated salt solution can be used as an initial wash to remove water from an organic solvent, with additional water removed from the organic solvent using magnesium sulfate ($MgSO_4$). In contrast, the saturated salt solution utilized in the methods of the present disclosure may be used to produce distinct organic and aqueous layers in a mixture that includes two miscible solvents, i.e., an aqueous solution and MeCN. Since water and MeCN are substantially miscible, conducting a liquid/liquid extraction on such a mixture is difficult. However, by adding the salt to saturate the aqueous layer of the mixture, the water and MeCN may separate into distinct aqueous and organic layers, which are then easily separated. The addition of the salt to the aqueous layer decreases the solubility of MeCN in the aqueous layer, this results in increasing the amount of PBA that partitions into the MeCN layer and therefore the amount of PBA that may be recovered. The ability to separate the aqueous and organic layers also improves the yield of the PBA or 4-chloro-2-fluoro-3-substituted-phenylboronic acid that may be obtained.

The following examples serve to explain embodiments of the present disclosure in more detail. These examples are not to be construed as being exhaustive or exclusive as to the scope of this invention.

EXAMPLES

Example 1

Isolation of PBA from MeCN 2,6-CFA (10.0 g, 62.28 mmol) was weighed in a separate flask and transferred to a 3-neck, 500-ml round bottom flask equipped with a thermocouple temperature probe, stir bar, and a $N_2$ inlet. The flask was rinsed with anhydrous DME. Additional DME was added to the reaction flask to give a total DME volume of 106 ml. The reaction was cooled to −78° C. with a dry ice/acetone bath. Once the reaction reached −77° C., n-BuLi (29 ml, 71.62 mmol, 2.5 M in hexanes) was added slowly, dropwise, using a syringe pump over a 45 minute period. The highest temperature reached during addition was −70.1° C. After complete addition of n-BuLi, the reaction was left to stir for 1 hour at −74.1° C. After 1 hour, $B(OMe)_3$ (10.5 ml, 93.42 mmol) was added dropwise using a syringe pump over a period of 22 minutes. The highest temperature reached during the $B(OMe)_3$ addition was −67.0° C. After the complete addition of $B(OMe)_3$, the dry ice/acetone bath was removed and the reaction mixture warmed to room temperature (approximately 23.1° C.). Once the reaction mixture reached room temperature, the reaction was left to stir an additional 1 hour at that temperature. Using an addition funnel, 1N NaOH (aq) (78 ml, 77.85 mmol) was added dropwise to the reaction mixture. After complete addition, the reaction mixture was stirred for 1 hour at room temperature. The reaction mixture was then transferred to a 500-ml separatory funnel and the layers separated. The aqueous layer was washed with TBME (2×75 ml) to remove unwanted impurities and/or unreacted 2,6-CFA. The aqueous layer was then acidified with 6 N HCl (aq) (42 ml, 249.1 mmol) and extracted with MeCN (3×75 ml). When the first volume (75 ml) of the MeCN was added, the aqueous layer and organic layer distinctly separated. Solid NaCl was added to the MeCN/water mixture to ensure the aqueous layer was saturated with salt, and the distinct aqueous and organic layers separated. Two additional volumes of 75 ml of MeCN were added and the distinct aqueous and organic layers separated. The organic layers were combined, dried with magnesium sulfate ($MgSO_4$), and filtered into a 500 ml round bottom flask. To determine the yield of the reaction, the PBA solution in MeCN was concentrated to dryness under reduced pressure. The white solid was further dried in a vacuum oven at 55° C. to give 11.4 g (90% yield) of PBA.

Example 2

Alternate Isolation of PBA from MeCN 2,6-CFA (10.0 g, 62.28 mmol) was weighed in a separate flask and transferred to a 3-neck, 500-ml round bottom flask equipped with a thermocouple temperature probe, stir bar, and a $N_2$ inlet. The flask was rinsed with anhydrous DME.

Additional DME (total volume of 106 ml) was added to the reaction. The reaction was cooled to −78° C. with a dry ice/acetone bath. Once the reaction reached approximately −77° C., n-BuLi (29 ml, 71.62 mmol, 2.5 M in hexanes) was slowly added dropwise using a syringe pump over a 45 minute period. The highest temperature reached during addition was −70.1° C. After complete addition of n-BuLi, the reaction was left to stir for 1 hour at −72.1° C. After 1 hour, B(OMe)$_3$ (10.5 ml, 93.42 mmol) was added dropwise using a syringe pump over a period of 22 minutes. The highest temperature reached during the addition was −67.0° C. After complete addition of B(OMe)$_3$, the dry ice/acetone bath was removed and the reaction mixture was warmed to room temperature overnight. The next morning, the reaction mixture temperature was at 22.7° C. Using an addition funnel, 1N NaOH (aq) (78 ml, 77.85 mmol) was added dropwise to the reaction mixture. After complete addition, the reaction mixture was stirred for 1.5 hours at room temperature. The reaction mixture was then transferred to a 500-ml separatory funnel and the organic and aqueous layers separated. The aqueous layer was washed with TBME (2×75 ml) to remove unwanted impurities and/or unreacted 2,6-CFA. The aqueous layer was acidified with 6N aqueous HCl (42 ml, 249.1 mmol) and then MeCN (3×75 ml) added. Since water and MeCN are miscible, the two distinct layers were not distinguishable. Solid NaCl was then added to saturate the aqueous layer, which resulted in the formation of two distinct layers: the MeCN layer and the aqueous layer, which were separated. The organic layers were combined, dried with MgSO$_4$, and filtered into a 500-ml round bottom flask. To determine the yield of the reaction, the PBA solution in MeCN was concentrated to dryness under reduced pressure. The white solid was further dried in a vacuum oven at 55° C. to give 11.8 g (93% yield) of PBA.

Example 3

Alternate Isolation of PBA from MeCN 2,6-CFA (10.0 g, 62.28 mmol) was weighed in a separate flask and transferred to a 3-neck, 500-ml round bottom flask equipped with a thermocouple temperature probe, stir bar, and a N$_2$ inlet. The flask was rinsed with anhydrous DME. Additional DME (total volume of 106 ml) was added to the reaction. The reaction was cooled to −78° C. with a dry ice/acetone bath. Once the reaction reached approximately −72.7° C., n-BuLi (29 ml, 71.62 mmol, 2.5 M in hexanes) was slowly added dropwise using a syringe pump over a 45 minute period. The highest temperature reached during addition was −71.5° C. After complete addition of n-BuLi, the reaction was left to stir for 1 hour at −71.5° C. After 1 hour, B(OMe)$_3$ (10.5 ml, 93.42 mmol) was added dropwise using a syringe pump over a period of 22 minutes. Temperature during addition was kept below −65° C. After complete addition of B(OMe)$_3$, the dry ice/acetone bath was removed and the reaction mixture was warmed to room temperature overnight. The next morning, the reaction mixture temperature was at 24.9° C. Using an addition funnel, 1N NaOH (aq) (78 ml, 77.85 mmol) was added dropwise to the reaction mixture. After complete addition, the reaction mixture was stirred for 1.5 hours at room temperature. The reaction mixture was then transferred to a 500-ml separatory funnel and the layers separated. The aqueous layer was washed with TBME (2×75 ml) to remove unreacted 2,6-CFA. The aqueous layer was acidified with 6N aqueous HCl (42 ml, 249.1 mmol). Initially, 100 mL of MeCN was added to the aqueous mixture and shaked. Since water and MeCN are miscible, two distinct layers were not distinguishable. A brine solution (approximately 25 wt % sodium chloride in water) was added to saturate the aqueous layer, which resulted in the formation of two distinct layers: the MeCN layer and the aqueous layer, which were separated. The aqueous layer was extracted with MeCN (2×75 mL). The organic layers were combined, dried with MgSO$_4$, and filtered into a 500-ml round bottom flask. To determine the yield of the reaction, the PBA solution in MeCN was concentrated to dryness under reduced pressure. The white solid was further dried in a vacuum oven at 55° C. to give 11.3 g (89% yield) of PBA.

Example 4

Comparative Example

A solution of 2,6-CFA (9.6 g) in anhydrous DME (75 ml) was prepared in a 100-ml, 3-neck flask equipped with a magnetic stirrer, thermowell with thermocouple temperature probe, a rubber septum, and a condenser with a N$_2$ inlet. The solution was stirred and cooled to −71.0° C. using a dry ice/acetone bath. A solution of n-BuLi (31.5 ml of 2.5 M butyllithium in hexanes) was added slowly over 1.57 hours using a syringe pump, maintaining the reaction temperature below −65° C. The reaction mixture was stirred for 20 minutes at a temperature of from −72.0° C. to 73.4° C., then B(OMe)$_3$ (10.5 ml) was added slowly over 43 minutes using a syringe pump, maintaining the temperature below −65° C. Upon completion of the B(OMe)$_3$ addition, the reaction mixture was allowed to slowly warm to ambient temperature overnight. A solution of KOH in water (133 ml of 5.6% aqueous KOH, approximately 1 M) was added to the reaction mixture at room temperature (approximately 23.1° C.) over 17 minutes using an addition funnel. The mixture was stirred for 60 minutes, and then was transferred to a separatory funnel where the organic and aqueous layers were allowed to separate. The aqueous layer was washed with TBME (2×73 ml) to remove unreacted 2,6-CFA. The aqueous layer was then transferred to a 250-ml Erlenmeyer flask, extracted with MeCN (76 ml), and acidified by the dropwise addition of 6 M aqueous HCl (40 ml). The organic layer (27.87 g) was separated and found to contain 5.00 g of PBA by GC assay. The aqueous layer was extracted with additional acetonitrile (2×76 ml) and the two additional organic layers (24.88 g and 156.48 g) were likewise assayed. The total recovered product in MeCN was 9.85 g (80.3% yield). While a solution of KOH was used as the aqueous base in this experiment, no difference in the yield of PBA was found when a solution of NaOH was used.

While the invention may be susceptible to various modifications and alternative forms, specific embodiments have been described by way of example in detail herein. However, it should be understood that the invention is not intended to be limited to the particular forms disclosed. Rather, the invention is to cover all modifications, equivalents, and alternatives falling within the scope of the invention as defined by the following appended claims and their legal equivalents.

What is claimed is:

1. A method of isolating a 4-chloro-2-fluoro-3-methoxyphenyl-boronic acid, comprising:
    saturating a mixture of water, acetonitrile, and a 4-chloro-2-fluoro-3-methoxyphenyl-boronic acid with a salt to form an acetonitrile layer and a water layer;
    partitioning the 4-chloro-2-fluoro-3-methoxyphenyl-boronic acid into the acetonitrile layer;
    separating the acetonitrile layer comprising the 4-chloro-2-fluoro-3-methoxyphenyl-boronic acid from the water layer;

utilizing the 4-chloro-2-fluoro-3-methoxyphenyl-boronic acid in the acetonitrile for a Suzuki coupling reaction without concentration or isolation acts.

2. A method of isolating a 4-chloro-2-fluoro-3-substituted-phenylboronic acid, comprising:
adding a salt to an acetonitrile/water mixture comprising a 4-chloro-2-fluoro-3-substituted-phenylboronic acid to saturate the acetonitrile/water mixture;
partitioning the 4-chloro-2-fluoro-3-substituted-phenylboronic acid into an acetonitrile layer;
separating the acetonitrile layer comprising the 4-chloro-2-fluoro-3-substituted-phenylboronic acid from a water layer; and
utilizing the 4-chloro-2-fluoro-3-substituted-phenylboronic acid in the acetonitrile for a synthesis of a herbicidal compound without concentration or isolation acts.

3. The method of claim 2, wherein adding a salt to an acetonitrile/water mixture comprising a 4-chloro-2-fluoro-3-substituted-phenylboronic acid comprises adding a saturated salt solution to the acetonitrile/water mixture.

4. The method of claim 2, wherein adding a salt to an acetonitrile/water mixture comprising a 4-chloro-2-fluoro-3-substituted-phenylboronic acid comprises adding a saturated sodium chloride solution to the acetonitrile/water mixture.

5. The method of claim 2, wherein adding a salt to an acetonitrile/water mixture comprising a 4-chloro-2-fluoro-3-substituted-phenylboronic acid comprises adding a solid salt to the acetonitrile/water mixture.

6. The method of claim 2, wherein adding a salt to an acetonitrile/water mixture comprising a 4-chloro-2-fluoro-3-substituted-phenylboronic acid comprises adding solid sodium chloride to the acetonitrile/water mixture.

7. The method of claim 2, wherein adding a salt to an acetonitrile/water mixture comprises adding a salt selected from the group consisting of sodium chloride, potassium chloride, calcium chloride, sodium bromide, potassium bromide, sodium sulfate, potassium sulfate, ammonium chloride, and combinations thereof.

8. A method of synthesizing and isolating 4-chloro-2-fluoro-3-methoxyphenylboronic acid, comprising:
contacting 2-chloro-6-fluoroanisole (2,6-CFA) with n-butyl lithium to form a lithiated derivative of 2,6-CFA;
contacting the lithiated derivative of 2,6-CFA with $B(OCH_3)_3$ to form a boronic acid ester of 2,6-CFA;
contacting the boronic acid ester of 2,6-CFA with aqueous sodium hydroxide to form a sodium salt of the boronic acid of 2,6-CFA;
contacting the sodium salt of the boronic acid of 2,6-CFA with aqueous hydrochloric acid to form a solution of 4-chloro-2-fluoro-3-methoxyphenylboronic acid;
adding acetonitrile to the solution of 4-chloro-2-fluoro-3-methoxyphenylboronic acid to form a mixture of acetonitrile, water, and 4-chloro-2-fluoro-3-methoxyphenylboronic acid;
adding a salt to the mixture of acetonitrile, water, and 4-chloro-2-fluoro-3-methoxyphenylboronic acid to saturate the mixture and form an acetonitrile layer and a water layer, the 4-chloro-2-fluoro-3-methoxyphenylboronic acid partitioning to the acetonitrile layer;
separating the acetonitrile layer and the water layer; and
using the 4-chloro-2-fluoro-3-methoxyphenylboronic acid in the acetonitrile for a synthesis of a herbicidal compound without concentration or isolation acts.

9. The method of claim 8, wherein adding a salt to the mixture of acetonitrile, water, and 4-chloro-2-fluoro-3-methoxyphenylboronic acid comprises adding solid sodium chloride to the mixture.

10. The method of claim 8, wherein adding a salt to the mixture of acetonitrile, water, and 4-chloro-2-fluoro-3-methoxyphenylboronic acid comprises adding a saturated solution of sodium chloride to the mixture.

11. The method of claim 8, wherein adding a salt to the mixture of acetonitrile, water, and 4-chloro-2-fluoro-3-methoxyphenylboronic acid comprises adding a salt selected from the group consisting of sodium chloride, potassium chloride, calcium chloride, sodium bromide, potassium bromide, sodium sulfate, potassium sulfate, ammonium chloride, and combinations thereof.

12. The method of claim 8, wherein using the 4-chloro-2-fluoro-3-methoxyphenylboronic acid in the acetonitrile for a synthesis of a herbicidal compound without concentration or isolation acts comprises utilizing the 4-chloro-2-fluoro-3-methoxyphenylboronic acid in the acetonitrile for in a Suzuki coupling reaction without concentration or drying.

13. The method of claim 8, wherein using the 4-chloro-2-fluoro-3-methoxyphenylboronic acid in the acetonitrile for a synthesis of a herbicidal compound without concentration or isolation acts comprises using the 4-chloro-2-fluoro-3-methoxyphenylboronic acid in the acetonitrile without concentration or drying for a synthesis of 6-(4-chloro-2-fluoro-3-methoxyphenyl)-4-aminopicolinate or 2-(4-chloro-2-fluoro-3-methoxy phenyl)-6-amino-4-pyrimidinecarboxylic acid.

14. The method of claim 1, wherein saturating a mixture of water, acetonitrile, and a 4-chloro-2-fluoro-3-methoxyphenyl-boronic acid with a salt comprises saturating the mixture with a salt selected from the group consisting of sodium chloride, potassium chloride, calcium chloride, sodium bromide, potassium bromide, sodium sulfate, potassium sulfate, ammonium chloride, and combinations thereof.

15. The method of claim 1, wherein utilizing the 4-chloro-2-fluoro-3-methoxyphenyl-boronic acid in the acetonitrile for a Suzuki coupling reaction without concentration or isolation acts comprises using the 4-chloro-2-fluoro-3-methoxyphenyl-boronic acid in the acetonitrile for a synthesis of 6-(4-chloro-2-fluoro-3-methoxyphenyl)-4-aminopicolinate or 2-(4-chloro-2-fluoro-3-methoxyphenyl)-6-amino-4-pyrimidinecarboxylic acid.

16. The method of claim 2, wherein utilizing the 4-chloro-2-fluoro-3-substituted-phenylboronic acid in the acetonitrile for a synthesis of a herbicidal compound without concentration or isolation acts comprises using the 4-chloro-2-fluoro-3-substituted-phenylboronic acid in the acetonitrile in a Suzuki coupling reaction.

17. The method of claim 2, wherein utilizing the 4-chloro-2-fluoro-3-substituted-phenylboronic acid in the acetonitrile for a synthesis of a herbicidal compound without concentration or isolation acts coin rises using the 4-chloro-2-fluoro-3-substituted-phenylboronic acid in the acetonitrile for a synthesis of 6-(4-chloro-2-fluoro-3-substituted-phenyl)-4-aminopicolinate or 2-(4-chloro-2-fluoro-3-substituted-phenyl)-6-amino-4-pyrimidine carboxylic acid.

* * * * *